(12) United States Patent
Hayman et al.

(10) Patent No.: US 7,887,475 B1
(45) Date of Patent: Feb. 15, 2011

(54) COMPUTER SEARCHABLE ANATOMICAL DATABASE AND VISUAL KEY

(75) Inventors: Linda Anne Hayman, Houston, TX (US); Dianne Dulla, Houston, TX (US); John J. Pagani, IV, Dallas, TX (US); Mark Vabulas, Dallas, TX (US)

(73) Assignee: ANATOM-e, L.L.C., Houston, TX (US)

( * ) Notice: Subject to any disclaimer, the term of this patent is extended or adjusted under 35 U.S.C. 154(b) by 1685 days.

(21) Appl. No.: 11/038,448

(22) Filed: Jan. 19, 2005

(51) Int. Cl.
*A61N 5/00* (2006.01)
(52) U.S. Cl. .......................................... 600/1
(58) Field of Classification Search ................. 600/300, 600/1–8; 128/897, 898, 920–924
See application file for complete search history.

(56) References Cited

U.S. PATENT DOCUMENTS

| | | | | |
|---|---|---|---|---|
| 3,962,807 | A * | 6/1976 | Pantone | 40/371 |
| 6,115,717 | A * | 9/2000 | Mehrotra et al. | 707/102 |
| 6,301,329 | B1 * | 10/2001 | Surridge | 378/65 |
| 6,418,430 | B1 * | 7/2002 | DeFazio et al. | 707/3 |
| 6,978,166 | B2 * | 12/2005 | Foley et al. | 600/425 |
| 7,317,816 | B2 * | 1/2008 | Ray et al. | 382/118 |
| 2005/0027570 | A1 * | 2/2005 | Maier et al. | 705/3 |
| 2006/0110036 | A1 * | 5/2006 | Luo et al. | 382/170 |

* cited by examiner

*Primary Examiner*—Samuel G Gilbert
(74) *Attorney, Agent, or Firm*—D. Arlon Groves

(57) ABSTRACT

A pictorially searchable anatomical database with computer assisted mapping is presented. The pictorial portion of the database and the textual portion of the database are fully unified, i.e., all elements are "live" and visually navigating through one will instantaneously display the corresponding element of the other. A "standard reference" and unique visual keys are presented; selection of a structure of interest may be displayed both in the form of a conventional two-dimensional scan and a three-dimensional view of the structure of interest; all structures in both the 2-D and 3-D views may be interrogated. In addition, structures connected to the structure of interest may likewise be displayed in both the two- and the three-dimensional views. While the inclusive database will be of utility to a variety of physicians, including first responders, clinicians, surgeons and diagnosticians, it will be of particular utility to radiation treatment planners: a patient's images may be imported onto the display screen of the present invention and superimposed upon or merged with the standard reference images of the present invention for more accurate and more rapid delineation of structures to be treated or avoided.

69 Claims, 10 Drawing Sheets

COMPUTER SEARCHABLE ANATOMICAL DATABASE AND VISUAL KEY

BACKGROUND OF THE INVENTION

This invention has important benefits to both the first responders of the medical community, i.e., those who must first see, on an urgent basis, victims of trauma or of nuclear, biological or chemical accidents or attacks, and to those who desire to use it, on a more considered basis, as a reference tool to aid their treatment of a wide variety of illnesses.

Surprising though it may be to both the scientific community and to the lay public in general, there is, even at this late date, incomplete agreement among medical professionals as to the names of the various body parts, as to the types of various body parts, and even as to the functions of various body parts. A careful review of the medical literature will establish that there are, in general, at least three different systems for naming body parts, namely, one followed by the anatomists, another by the surgeons, and yet another by the clinicians. It is not at all uncommon to find three (or more) different names for the same body part, and, worse yet, all too often a common name may be used by the different practitioners for different body parts. The possibilities for confusion, and medical errors, are enormous.

Although not so extensive as the naming differences, in far too many instances there is no agreement as to what kind of body part a specific part may be, nor as to the 'real' function of such body parts. As but one illustration, doctors who believe that a specific body part situated near a tumor is a lymph node may elect to irradiate or remove that body part at the same time that the tumor is treated, while doctors who do not believe that that body part is a lymph node probably will not treat it at that time. Thus widely different outcomes may be realized by different patients with identical conditions, just because their respective physicians hold differing opinions as to what type of body part a particular part is, and what its 'true' function may be.

Hundreds if not thousands of anatomical texts or reference works are presently available to researchers, or, at least, are available in medical libraries scattered throughout the world. A first responder, of course, presented with an injury other than one of the run-of-the-mill variety, simply does not have enough time to search for the reference which may be the most authoritative for that particular injury; even if he happened to have the particular text on his shelf, it is highly doubtful that he would have the time to actually consult it. And, of course, in the present state of the art, what one does not possess, one cannot consult. At first glance, the diagnosing and treating physicians may be thought to be in a better position, having the luxury of more time, but all too often their situation is scarcely better; with governmental limitations on radiologists, for example, a radiologist typically has just a few minutes—nearly always fewer than ten—in which to both read the images in question and dictate his conclusions. Formerly, it was typical for a radiologist to have only a few images per patient to read; now, it is common for a few hundred images, per patient, to be taken, leaving the radiologists with ever less time to spend on each image. Although the treating physicians may not be so rushed as the radiologists, the realities of daily practice, including the economic need to push patients through as rapidly as possible, inevitably result in little or no time to consult a number of references, many of which are not even widely available. While the system works well enough for the garden variety of problems which physicians see most frequently, it tends to break down when rare or even less common ailments are presented.

The federal government has undertaken an expensive effort, known as the Visible Human Project, to partially alleviate this problem, but its efforts to date seem to have been misdirected. At a cost in excess of a million dollars, it has frozen a human male and a female cadaver and then sliced them, reportedly at intervals of one millimeter, into over eighteen hundred slices, and photographed each slice. The results are available on the internet, but, regrettably, are of only limited utility. Only the anatomists' system for naming body parts is utilized, with no correlation to the different nomenclature systems, so the confusion of body parts is thus not alleviated. Further, one cannot locate an image of a particularly desired body part by simply typing in a name and allowing the program to search for the body part corresponding to that name. In order to locate images of a particular body part relatively quickly, the user must know both the approximate location of the body part and approximately what it looks like; the pertinent image or 'slice' may have in excess of fifty names of body structures surrounding the image, each with a black line running to the appropriate structure, and the names are not presented in alphabetical order but by geometrical convenience. Should a user not know the approximate location, the user may expend a great amount of time in searching for its location. But even finding the structure of interest conveys very little useful information to the user: all that the user is presented with is a set of photographic images of dessicated body parts, in thin slices, which are of little real value to the vast majority of practicing physicians. Applicants know of no clinical physicians who actually use the Visible Human database, simply because of the great difficulty in translating from cadaver images to diagnostic or reference imagery, and because the nomenclature is so often not clinically relevant.

Some treating physicians, such as radiotherapy treatment planning physicians, have available to them a computer system which can receive sets of patient images via the PACS system and display them, perhaps even rotate them at will, on an associated computer monitor. While this promotes greater visual clarity and permits easier physical handling than the long-conventional method of developing negatives of film and then viewing them by shining a light through from underneath, with regard to the actual treatment planning it is hardly advanced over the old-fashioned film-viewing method: neither method alleviates a long-standing communications problem between diagnosing and treating physicians. In both instances the images will almost certainly have been read previously by a radiologist, whose report may have identified a probable tumor in a specific body part, by name. If the body part is a familiar one to the treatment planning physician, all is well and good, but if the part is not a commonly known body part or is unfamiliar to the planning physician, problems are immediately presented. First is the problem of just which body part image is the one at issue; the name employed by the radiologist may be unfamiliar to the treatment planner, or may refer to a different body part than the one of that same name known by the planner. After—it is hoped—having successfully resolved that problem, the planner is immediately confronted with yet another: what does that body part do; is it a critical body part, or can it be eliminated or have its function diminished? It is not at all uncommon, for the less common body parts, for discussions among the treatment planning team to ensue for hours, frequently involving telephone consultation with the reading radiologist, before these questions are resolved. And then, quite commonly, the same questions must be asked and answered about much of the surrounding tissue before the treatment planners can plan one or more paths for the treating radiation. After all this has been accomplished in the abstract, it still must be translated to the concrete before any actual treatment can begin. In particular, after all the arguments have been resolved, or at least after some form of consensus has been reached, a member of the treatment planning staff must still draw, in the computer system displaying the patient images, the outline of the body part or parts to be treated, on all images (or 'slices') in which the part or parts of interest appear. In many instances, then, a total of three to four hours—and all too often even more—can easily be consumed by the team of treatment planners in devising a treatment plan, which inevitably increases both the cost of treatment and the time required to get treatment underway.

SUMMARY OF THE INVENTION

The present invention is expected to revolutionize the practice of radiation therapy treatment and planning; to greatly assist first responders and other physicians in rapidly identifying the nature and function of affected body parts; and to increase both the speed and accuracy of treatment, thereby reducing the cost of treatment and minimizing the consequences of mistreatment. It is to be understood that the following summary of the invention is of a preferred embodiment only, and that many additional and/or different embodiments will readily suggest themselves to those skilled in the art without departing from the teachings or principles of the present invention. Also, the principles of the invention may have application in a number of fields beyond the medical field.

A preferred embodiment of the present invention may be considered as comprising at least two major components: a unified, computer searchable, anatomical database, and an appropriate computer system to quickly locate and graphically display the parts of interest. Preferably, the preferred embodiment will also permit a user to rapidly navigate through the pictorial display while instantaneously navigating through the textual database, and vice-versa. The preferred embodiment should also permit the displays to be manipulated at will.

In this instance, the invention may be best summarized by relating, in broad form, how a preferred embodiment was created. The creation of the unified, computer searchable anatomical database required more than a score of physician-years and a considerable total of computer-scientist-years. The body was divided into a number of major sub-portions, or regions, and teams of physicians spent years surveying, insofar as possible, the complete body of medical literature for each major region. Overly simplified, a typical approach—e.g., for the head and neck region—would be to first reduce the entire body of literature for each field into the fifty best references, then to the ten best, and then to the three best. Those not making these cuts, so to speak, were not simply discarded; in many instances, one or more of the non-final three might have the most authoritative description of a particular (and usually obscure) body part, which would be incorporated into the final database. Thus it is not accurate to describe the resulting database as merely a compilation of the three most authoritative reference works in each field; in each field, the number of sources is legion, although the amount from many sources may themselves be few in number. Further, it was found that the literature regarding other major regions could not be reduced to three primary references, but required some eight to ten primary references. The teaching of each selected source regarding a particular anatomical structure was then succinctly summarized or re-stated, as nearly as possible into a standard format, and the anatomical structure itself drawn and labelled, where necessary, according to one of the major nomenclature systems. The scope of the undertaking may be better understood by considering that, for the nervous system alone, several thousand separate anatomical structures had to be researched, summarized, drawn and labelled.

As may be inferred from the above, the unified, computer searchable, anatomical database may be considered to comprise two major sub-portions, a textual reference portion and a visual reference portion. The above description is primarily directed to the textual reference portion of a preferred embodiment. While for many applications a purely textual reference would be sufficient, particularly in view of the vast advance of applicants' textual reference over the state of the art, a visual reference unified with such a textual reference will be of even greater value to harried practitioners. In order to present critical information to the user in a form which is of the greatest benefit possible, several hundred clinically relevant images—in this instance computed tomographic images (CT's)—were taken of a live volunteer displaying primarily 'normal' anatomical structures. For a particular anatomical structure of interest, on each image displaying a 'slice' of that structure an outline is preferably drawn around the structure using an associated computer system that is particularly suited to such tasks. A preferred system will then develop a mathematical formula or utilize other mathematical means, such as the well-known Bezier techniques, to represent the usually irregularly shaped structure, so that the structure of interest may be recalled at will, may be displayed in either two-dimensional or three-dimensional form, and may be rotated, enlarged, shrunk or otherwise subjected to manipulations of interest. Applicants prefer to view structures of interest in three-dimensional form, but for many applications two-dimensional presentation may be sufficient. Continuing this procedure will, eventually, lead to completion of the visual reference portion.

To unify the textual and visual portions—i.e., to make each interactive with the other—applicants prefer to associate with each structure a large field for storing unique identifiers and other information of interest, which will permit each unique structure to be rapidly recalled in any of a variety of ways. One of the most common methods may be by typing in one of the names assigned to such structure, and identifying which naming system the user is utilizing, if known; a click of the cursor (or computer 'mouse'), or depression of a designated key on a keyboard, may then almost instantaneously present the structure of interest on an associated monitor. If the user informed the system of the nomenclature scheme being utilized, the first structure so displayed will be the correct structure; if he did not, then it may or may not be. If it is not, then a subsequent click or keystroke may almost instantaneously call up the second of such similarly named structures, which may be repeated as many times as necessary to find the anatomical structure of interest.

A preferred alternate method, or additional means of choice for the user, is to list, in alphabetical order, all anatomical structures by name (and by each nomenclature convention) and to allow a user to simply scroll down the list until the structure of interest is located, whereupon a click or keystroke may almost instantaneously present the reference image containing the desired structure for viewing, as previously described. Many users may prefer still another alternate method of initiating the viewing of a structure of interest.

The method of identifying images of patients—i.e., locating each 'slice' of a patient—has, fortunately, been semi-standardized for quite some time. In all systems known to applicants, the technician will position the first slice at either the top or bottom of an overall reference image and number each slice consecutively; usually only every fifth slice will be represented on the overall image, and such slices will be numbered in intervals of five, beginning with numeral one. Thus in some instances the numeral one will represent the topmost image, while in other instances it will represent the bottom image. Additionally, the exact position of a particular image—number one, say—even among technicians following the same convention will vary from technician to technician and, for the same technician, from patient to patient, but each image will always be consecutively numbered in one or the other convention and will be evenly spaced. Should the radiologist's report identify the slices' of interest by either of these standard nomenclature system, then a great deal of time on the part of the clinicians and the treatment planning physicians could be saved. Typing in the same identifier for applicants' standard reference images, or scrolling down a list of such and then clicking or keystroking, as described above, will virtually instantaneously present the corresponding standard reference image; a user may then direct the pointer to the structure of interest, and highlight it (or the highlighting may be accomplished automatically from the identifier selected, or on every structure as the pointer lands on each such structure, or by touching the screen) and then manipulate it as desired. It is most preferable to highlight a structure of interest with a touch of the pen, and to have the name of the structure automatically and simultaneously displayed on the screen in close proximity to the point of touching. It is next in order of preferability, or at least optionally, as each structure is sequentially being highlighted to have the corresponding textual information simultaneously be displayed on an adjacent portion of the screen; if not, it is next preferred to display such textual information upon a click on the highlighted structure, or upon a keyboard stroke while the structure of interest is so highlighted.

Yet another method of entry is possible, and while not necessary to practice other aspects of applicants' invention, is actually applicants' most preferred method. Applicants refer to this method as the visual key method. By this means, a recognizable image, such as a photograph or well-executed drawing, of a major body portion of a live human volunteer is superimposed upon a two-dimensional representation of the standard reference images (or vice-versa). In any event, it is preferred to impose yet more information, namely, a representation, preferably by differently colored sets of lines, of the standardized 'slices' of modern imagery, along with a presentation of major body systems for the major body portion under review. Others may prefer to have a composite image of only the human image and the standardized reference lines; in either event, the superposition(s) greatly enhance the practitioner's ability to quickly and accurately get to the body structure or structures of interest. By the liberal yet judicious use of color in a variety of ways, much more information, and information which is extremely beneficial, can be presented to the user in one convenient visual key. Others may prefer to use such a visual key in conjunction with a touch screen for rapid entry into the system.

Those planning radiation treatment will find it most convenient to have such a system as described herein closely adjacent to their treatment planning computer systems. Others may prefer to have their systems interconnected with the present system to the degree that patient images may be displayed on a split screen alongside applicants' reference images, while still others may prefer to overlay one upon the other. If so interconnected, a user may then use his planning system, and his cursor (or 'mouse'), or pen, to draw the structures to be treated (and those to be avoided) on the display screen of the present invention, with the certain knowledge that the correct structures have been identified for the appropriate treatment. Regardless of the option selected, the standard reference system of applicants' invention may then be used to help the treatment planners quickly and safely plan their treatment, and at much lower cost.

It is therefore an object of the present invention to provide an anatomical reference or database capable of handling inquiries in a multiplicity of nomenclature systems.

It is also an object of the present invention to provide an anatomical reference or database that is both complete and accurate for major body structures and systems, that may be presented in textual and/or graphical form, and whose detailed information is available virtually instantaneously.

It is yet a further object of the present invention to provide textual and graphical anatomical references which are unified with one another and which may be computer searchable either separately or jointly.

It is still another object of the present invention to provide a unified anatomical reference, the constituent parts of which may be accessed by multiple means.

It is a still further object of the present invention to display the reference images closely adjacent to the patient images, and to be able to overlay one upon the other.

It is yet another object to permit a treatment planning physician to be able to outline, in his own treatment planning computer system, the body parts to be treated or avoided, while such body parts are displayed on the monitor of the present system, in either an overlay or closely adjacent configuration.

These and other objects and features and advantages of the present invention will become apparent from the following detailed description, wherein reference is made to the accompanying drawings.

DETAILED DESCRIPTION OF THE PREFERRED EMBODIMENT

It is to be understood throughout this detailed description that the description is in no way to be taken as in any way limiting the scope or application of the present invention. Numerous embodiments and variations of the present invention will suggest themselves to those skilled in the art from a careful study of the aforementioned drawings and from understanding the principles and discoveries explained herein. In addition, it is to be understood that the details set forth in the following description are not in themselves limitations on the invention but merely details necessary to describe the embodiments of the invention preferred by the inventors.

Further, in describing the preferred manner of constructing a visual key for rapid and accurate entry into the database or into the patient images, it is to be understood that selection of the computed tomography (CT) scan form is only a preferred embodiment; applicants could just as well have used a nuclear magnetic resonance image (MRI), positron emission tomography (PET) scan, conventional X-ray image, ultrasound image, nuclear medical or other image, or even an artist's rendition. Also, since any single navigational setting is unlikely to be the most preferred for all cases, it should be understood that lateral and axial keys are preferably constructed as well, using the same principles of the present invention, although only the frontal key shall be described herein.

Still further, it is to be understood that the information and the computer system for handling and/or manipulating the information may reside in a purely local computer and be installed by means of a computer disc, or may reside in a server which may be located locally or remotely wherever desired, or in some combination thereof.

Additionally, it is to be understood that in the construction of visual keys there are many steps whose order is inconsequential; of more importance is the final visual key which may comprise one or more superpositions of various images or representations. Thus, for example, although construction of the present visual key is described as beginning with the CT scan, it could just as well have been described as beginning with an image or representation of the human volunteer.

Figure 1:
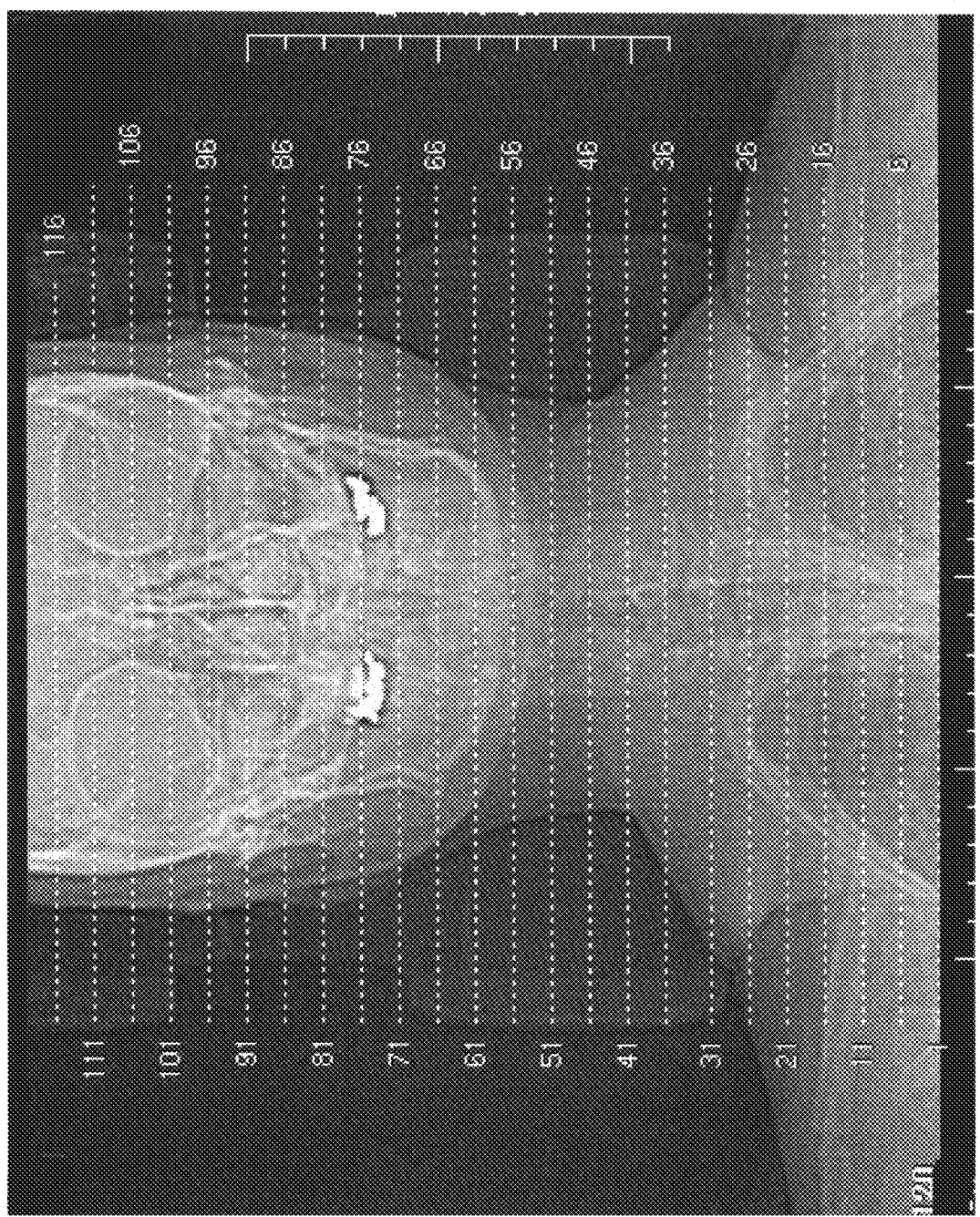
FIG. 1 is a frontal view of a computed tomographic image of a human volunteer, with standard reference lines (white, dashed).

FIG. 1 is a frontal view of a computed tomographic image (CT scan) of a human volunteer with the conventional equally spaced, white, dashed, horizontal reference lines, numbered in this example in intervals of five from 1 to 116. For clarity, only every fifth line is shown and numbered; these lines and numbers correspond to the levels which a medical technician has selected for the positioning of the axial sectional images of, again in this instance, the CT scan. Positioning and numbering of such sectional images is a standardized step in the process of taking such medical images, although some technicians will number the sectional images from the top down, and the precise locations of the sectional images or slices will vary from technician to technician and, even, from patient to patient for the same technician. Inclusion of such reference lines will allow the user to quickly navigate through the hundred or so (or hundreds of) sectional images by using the slice numbers on the final visual key. For example, any of lines 1-5 will produce a section at or near the bottom of the series of images, located in the chest, while any of lines 101 through 105 will produce a section near the top of the series, located in the orbit.

Figure 2:
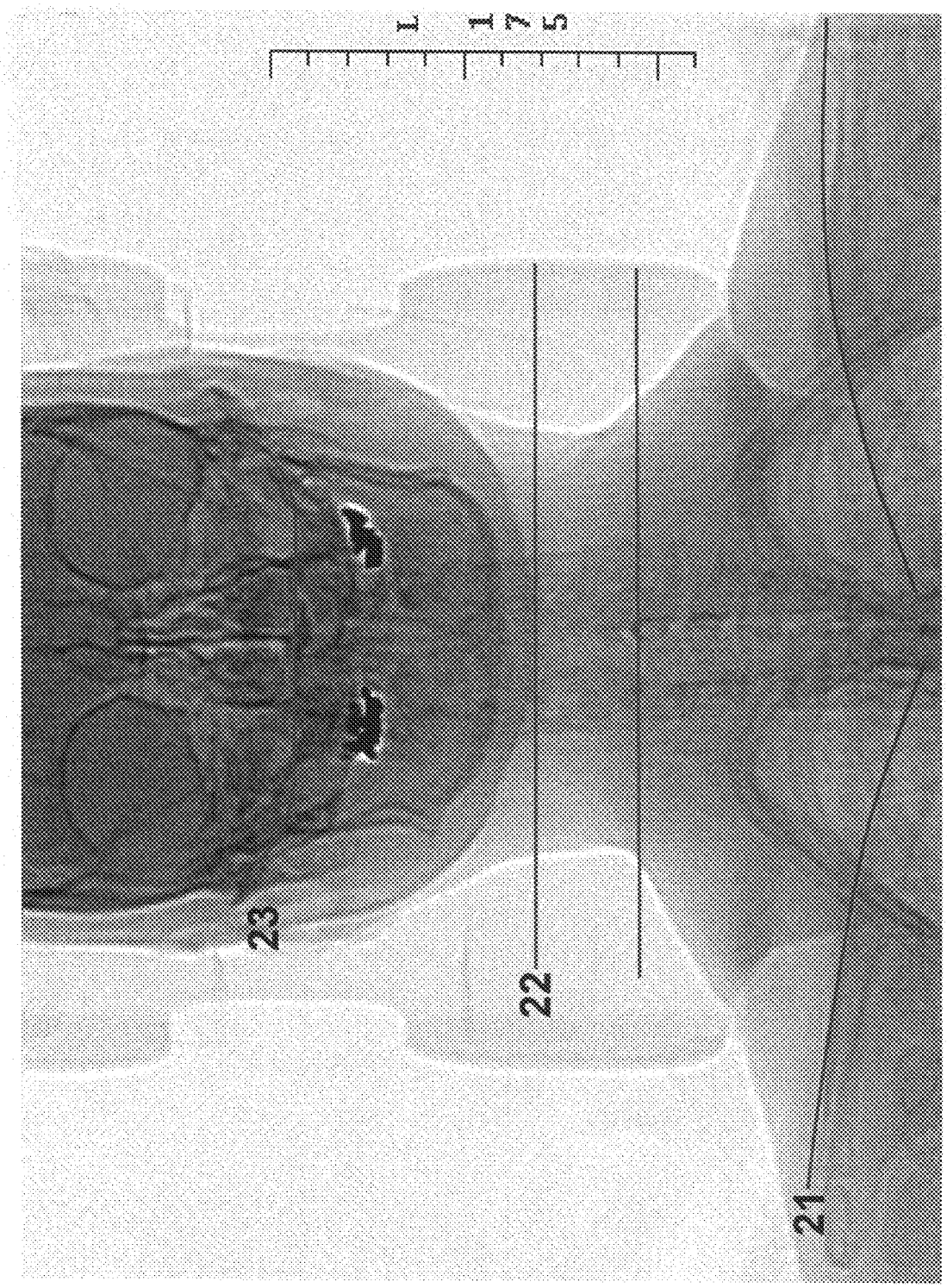
FIG. 2 is the same image as FIG. 1, but with the gray scale inverted, and with clinically relevant landmarks depicted as red lines.

Some views which are desired to comprise a portion of the final visual key may not always have sufficient clarity to accomplish this purpose. In that event, it may be desirable to enhance such an image, or, more precisely, enhance clinically relevant landmarks which can then be overlaid or superimposed upon the original image. FIG. 2 is the same image as FIG. 1, but in which the gray scale has been inverted, i.e., white replaced with black, black replaced with white, features with 40% black and 60% white replaced with 60% black and 40% white, etc.; the contrast may or may not need to be adjusted. Generally, such gray-scale inversion and contrast adjustment will permit clinically relevant landmarks, such as the collarbone, hyoid bone and skull base to be located with greater precision; such relevant landmarks are depicted in FIG. 2 as the red lines numbered 21, 22 and 23, respectively. After accurately positioning such landmarks, or other landmarks as may be desired, the landmark lines are incorporated into the image of FIG. 1; upon 'de-inversion,' the red landmark lines will appear as solid white lines, which applicants refer to as fiducial lines.

Figure 3:
FIG. 3 is a corresponding photograph of the volunteer whose images comprise the standard reference.
Figure 4:
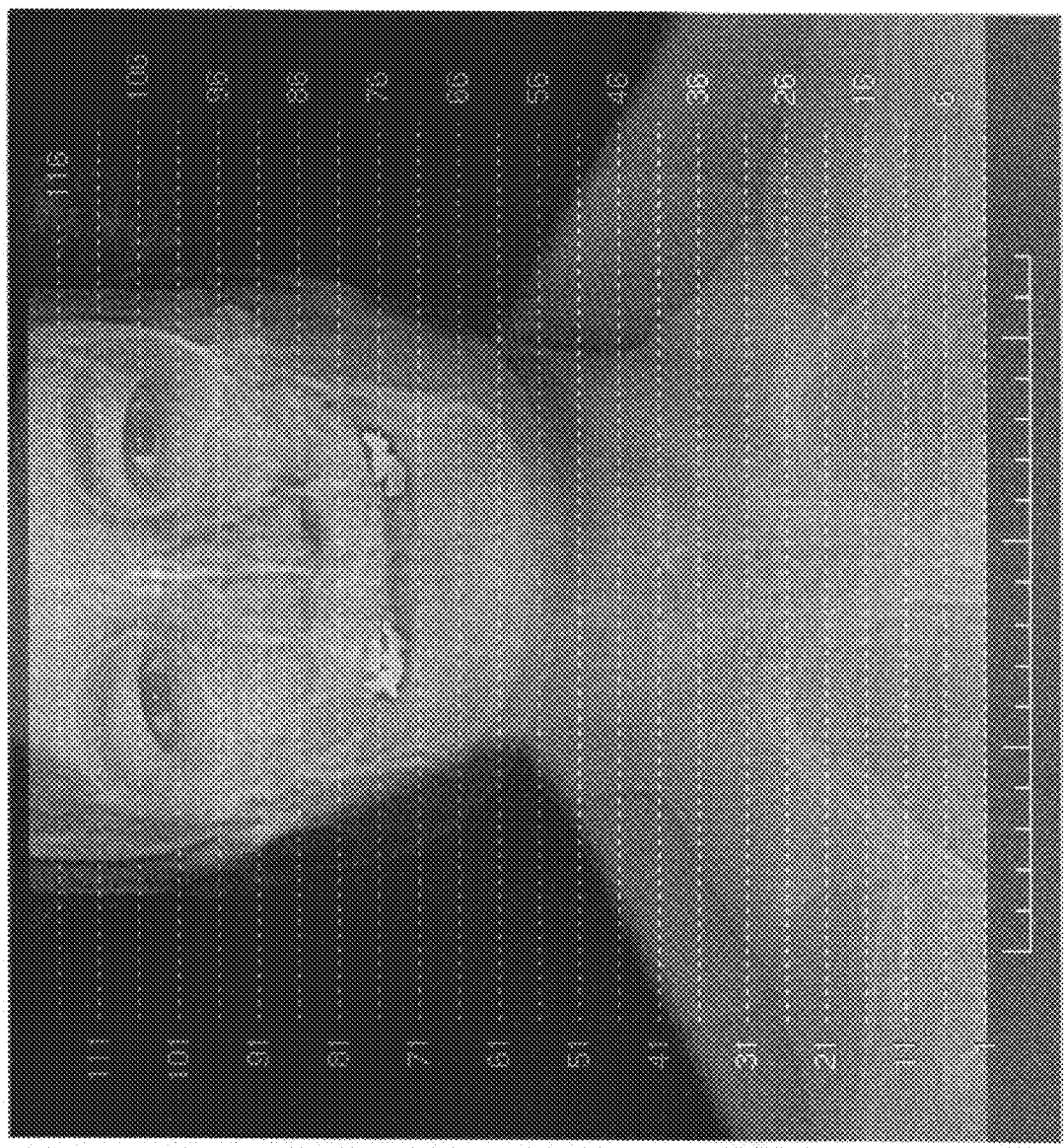
FIG. 4 is a screen print of the merged images of FIGS. 1 and 3, i.e., a composite in which one is overlayed upon the other.

FIG. 3 in this instance is a photograph of the outer surface of the human volunteer whose images comprise the standard reference. While an artist's rendering could be used, it is preferred to utilize an actual, digital photograph. In general it will be necessary to size the image to match the CT scans or other forms of images being used to construct the visual key. FIG. 4 is a merged combination of the partial visual key of FIG. 1 and the human representation of FIG. 3. It should be noted that providing an actual view of a human, or a high quality rendition, will permit not only more accurate navigation through the axial section images but in many instances will transmit such accurate information almost instantaneously. For example, for a patient with lesions at the corners of the mouth, such an improved visual key (even though FIG. 4 illustrates only a partially completed visual key) immediately informs the reader as to precisely which sections will show the regions of such lesions. Those skilled in the art will appreciate that the same result will be immediately obtainable for numerous other soft tissue regions.

Figure 5:
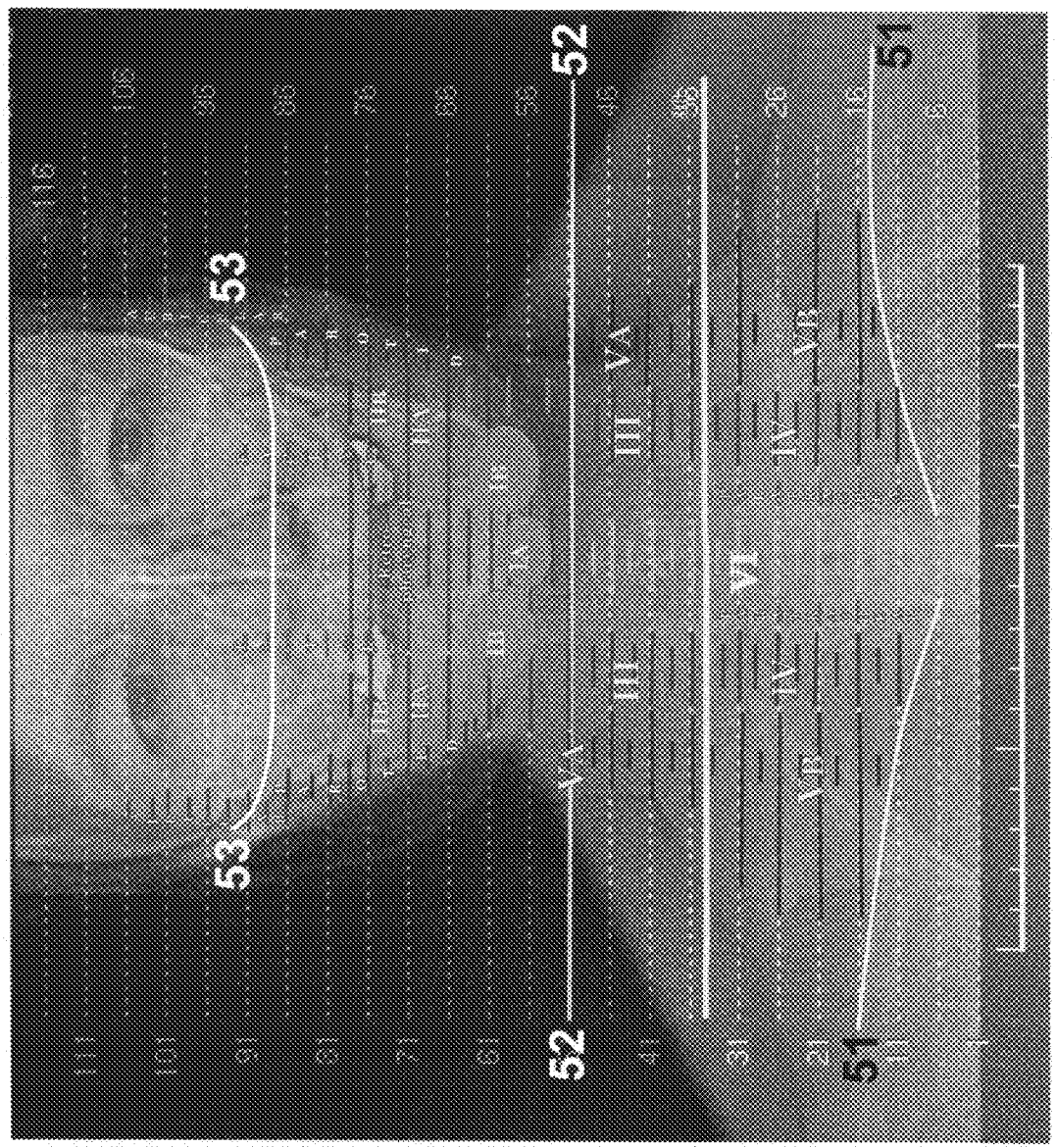
FIG. 5 is a completed version of one preferred visual key; i.e., FIG. 4 with dashed reference lines omitted for clarity and the addition of FIG. 6.
Figure 6:
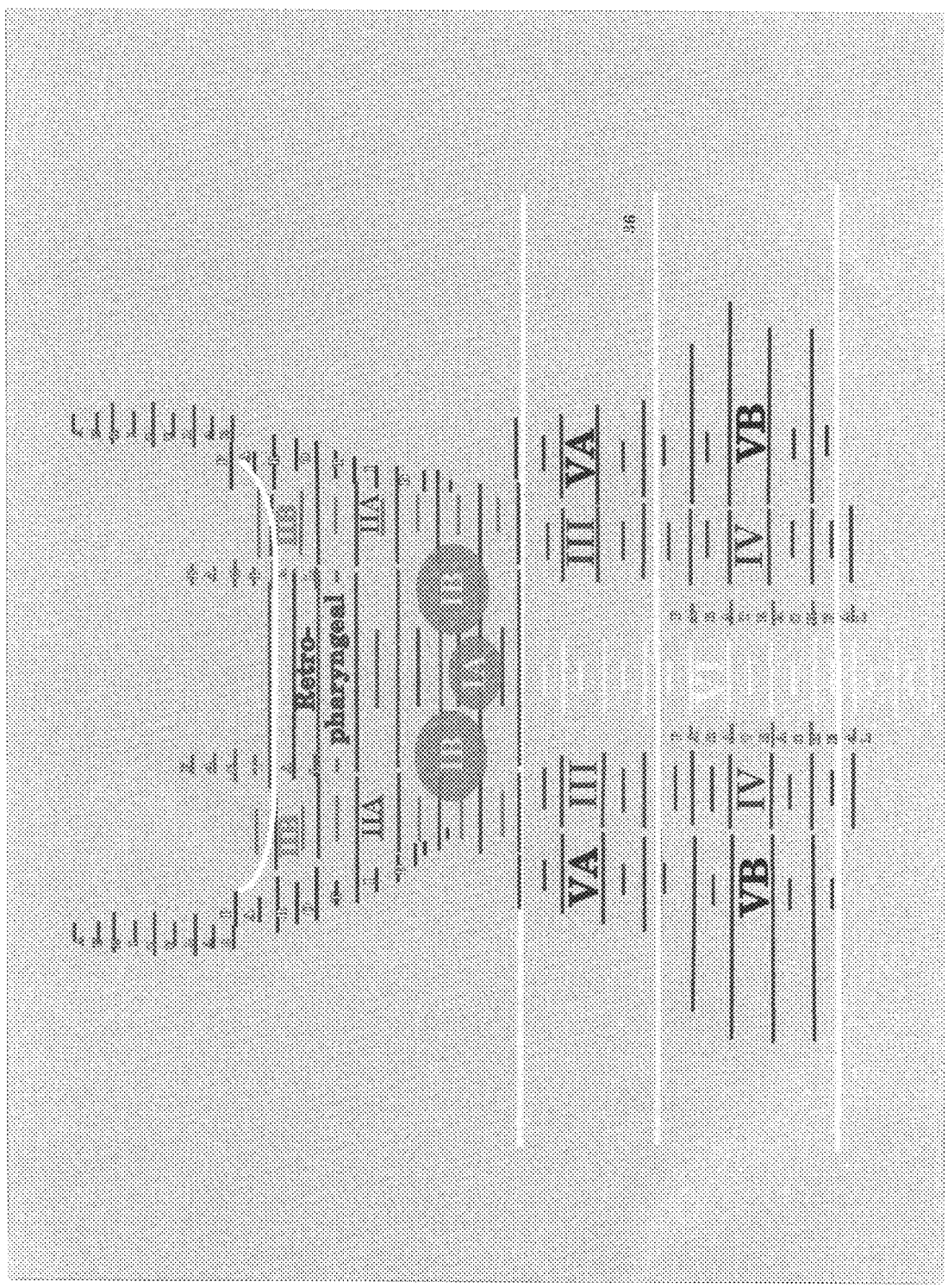
FIG. 6 separately depicts what was added to create FIG. 5, i.e., one of a number of partial keys which may be selected for addition to the composite figure of FIG. 4, preferably color coded and comprising clinically significant information.

FIG. 5 depicts a completed version of one preferred visual key, and is preferably constructed on the combined image of FIG. 4. For clarity and ease of explanation, FIG. 6 illustrates what has been added in FIG. 5. Those skilled in the art will appreciate that what has been added is clinically significant information and that, in fact, a large number of clinically important features can be added as may be desired. Those skilled in the medical arts will also recognize that what has been added for this visual key are the regions of the lymphatic system (which the art refers to as 'levels'); other clinically significant systems or structures may be similarly treated if desired. More particularly, the preferred key of FIG. 6 is a composite of the Rotterdam/Brussels Consensus (Roman numerals) and Richter system (names) for locating tissue containing lymph nodes.

Prior to explaining the use of color for the final key, it should perhaps be noted that the landmark lines depicted in the inverted image of FIG. 2 as the red lines 21, 22 and 23 appear, in the de-inverted image of FIG. 5, as the solid white fiducial lines 51, 52 and 53 (with the fiducial lines for the clavicle and the hyoid bone being shown in their more accurate curved form). For different landmarks, the reference lines may take on the form of boxes, circles, triangles or still other shapes. Applicants prefer to utilize such reference lines in a fixed or stationary mode, but others may prefer the option of having the positions of such reference lines adjustable. In any event, the use of such landmarks may not in all instances be strictly necessary, but applicants have determined that their use is frequently quite convenient and, therefore, such use is preferred. Similarly, the use of color for the final visual key may not be absolutely necessary but is highly preferred, as such use enables more information to be presented in a tightly confined space with clarity and without further obstructing the 'slice' lines of FIGS. 1 and 4.

For the head and neck region of the visual key under construction, the three differing major systems for classifying lymphatic systems—(i) Rotterdam/Brussels Consensus, (ii) E. Richter, and (iii) Rafael Martinez-Monge—may be conveniently illustrated with three different color schemes. The user may then determine which system he wishes to utilize, or he may quickly and conveniently compare one selected system with the others and then determine the system to be utilized. Rather than making a selection based only upon the particular system with which he may be most familiar, the user may make such selection on a more informed basis, thereby most likely obtaining a better outcome for the patient.

Figure 9:
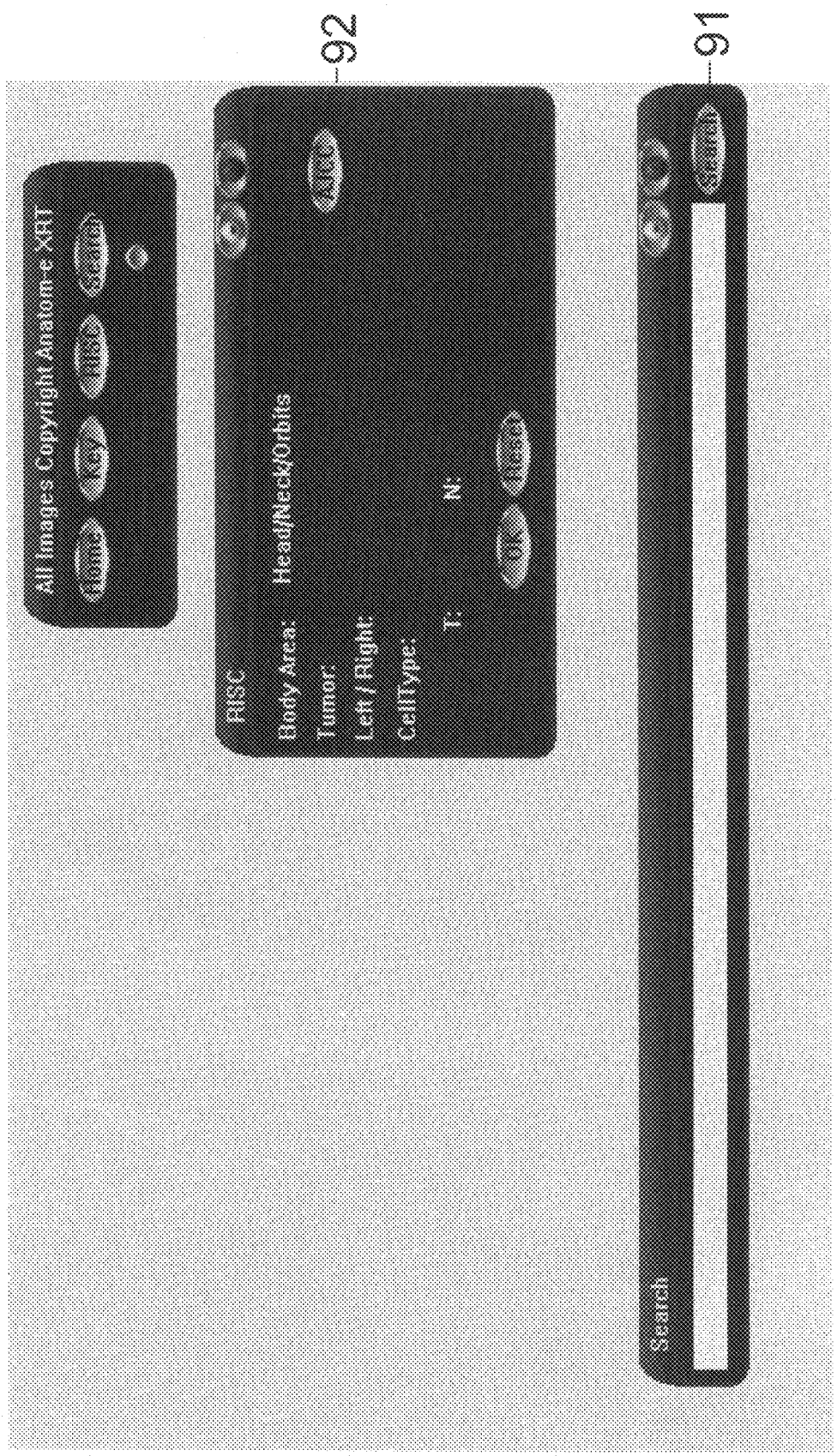
FIG. 9 is a screen print comprising a pair of drop-down menu windows which are particularly convenient for entry into the system.
Figure 10:
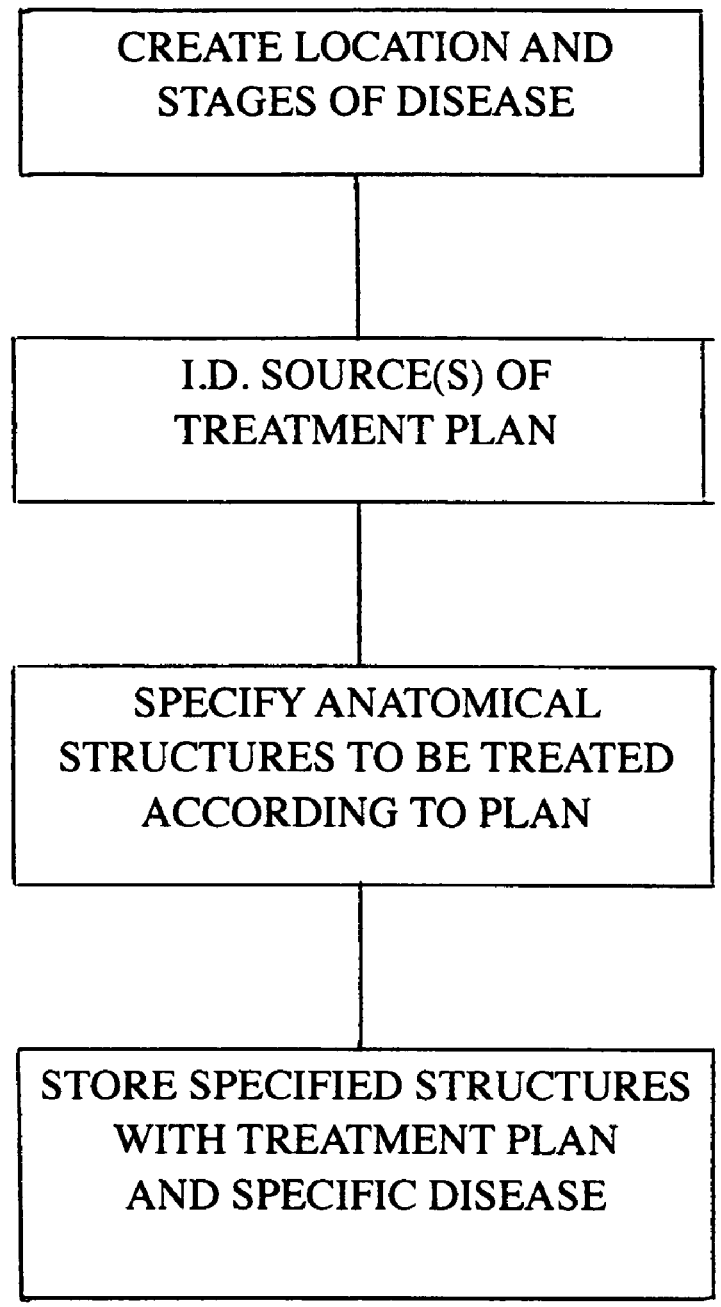
FIG. 10 is a block diagram depicting means for creating a computerized library.

As stated above, it is preferred to provide a number of means for entering the computer system. One convenient such means may be accomplished by a drop-down, preferably floating window 91 (FIG. 9) presented on a monitor or other viewer comprising a search slot, which may be utilized to provide two different means of entry. Initializing the search feature, in blank, may then produce a list of anatomical structures for the user to scroll through until the one of interest is located. In another means, a user may type into the search slot (or other designated location) the name of the anatomical structure of interest—a chore which may be alleviated somewhat by incorporating a smart auto-completion scheme. A preferred auto-completion scheme will not just merely complete entry of a name as soon as enough letters are entered for the name to be uniquely identifiable, but will also auto-complete from the general to the specific, as will be illustrated below.

Still other means of entry into the database may be accomplished through the pictorial or graphical portion of the database. One such means of entry permits the pictorial portion of interest to be called up for viewing upon just a minimal amount of manual entry of pertinent information. To accomplish this end, applicants prefer to utilize still another drop-down window 92; such a window may call for information as to (i) body area, (ii) preferred view (whether the presentation is to be of the left or right side of the body or of the midline, i.e., a combined view), (iii) tumor site and (iv) cell type (squamous, adenocarcinoma, etc.). It is also preferred for the user to be able to utilize the American Joint Commission on Cancer's classification system for tumors, and thus preferably the same drop-down window or panel may call for information as to tumor size (T-1, T-2, etc.) and nodal spread (N-1, N-2, etc.). Upon initializing a designated symbol, such as an "O.K." button, the preferred view of the images or 'slices'—such as element 71—may then be presented on the screen.

At this point still another drop-down window 72, preferably floating, may be presented on the monitor or viewer. It may be observed from the top row of said window that the Hard Palate was identified as the tumor site, Squamous as the type of cell, T1 as tumor size, and N2 as the level of nodal spread. It should be noted that not all tumors spread by means of the lymph system; some, such as those of the adenocystic cells, for example, spread by means of the nervous system. Had the user in the example illustrated specified Adenocystic as the type of cell of interest instead of Squamous, the pertinent portion of the nerve system would have been illustrated instead of a portion of the lymph system, and the various prompts on 72 for the nodal system would have been replaced by prompts for the nervous system. As may be seen from the second row of window 72, the Rotterdam/Brussels classification system for the lymphatic system was selected (green triangle pointed downward and appropriate prompts indented under the Rotterdam/Brussels heading); had one of the other two conventions been selected, the green triangle in front of either the Richter or the Martinez-Monge heading would have been rotated, and the prompts would appear under the appropriate heading. As may also be seen from the first two columns, the user was more interested in viewing various lymph nodes on the right side of the standard reference than on the left side.

Figure 8:
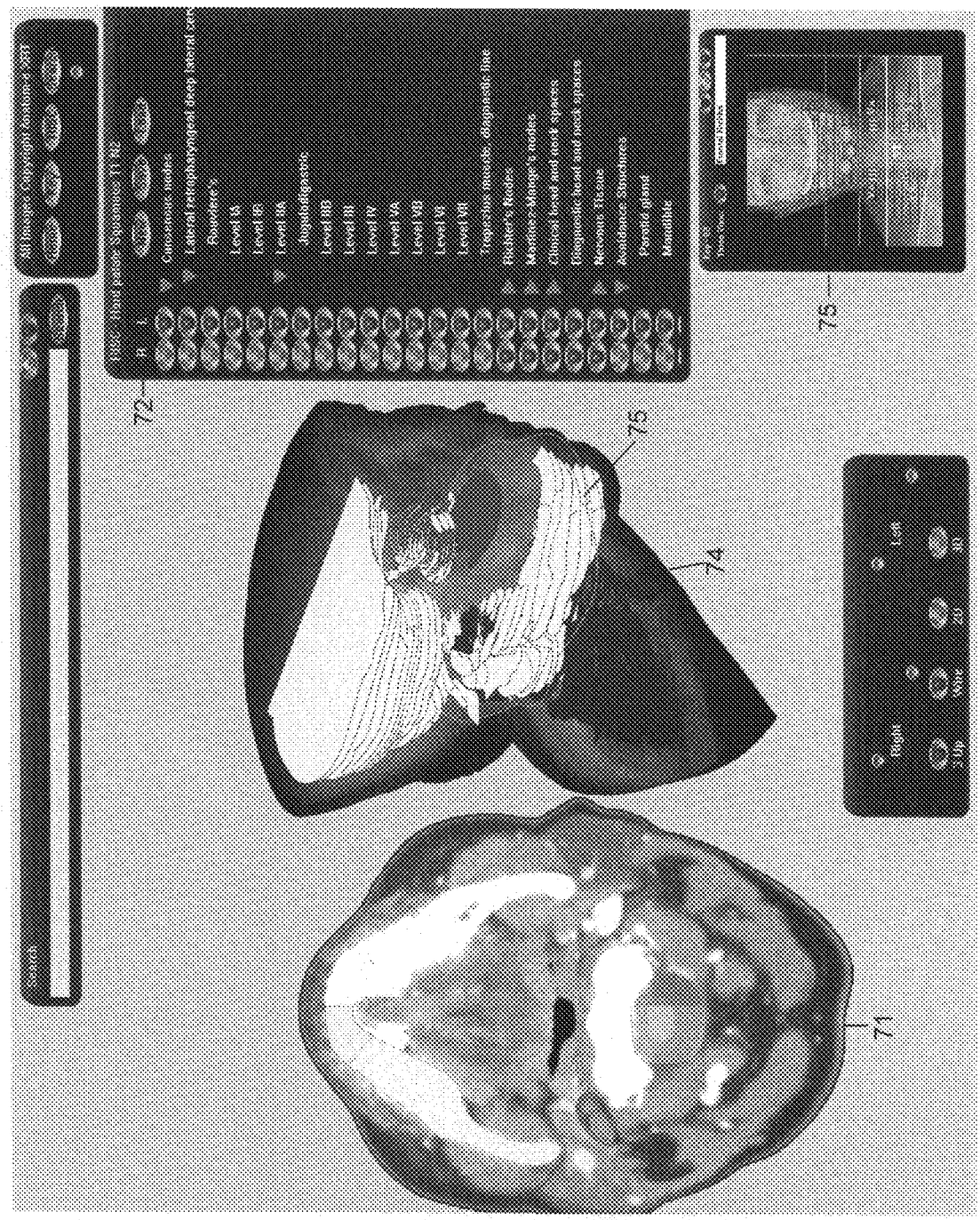
FIG. 8 is a screen print comprising a three dimensional representation of lymphatic tissue in the head and neck region, partial right view.

Yet another drop-down window 73 preferably calls for the user to specify whether it is desired to view the selected structures from the subject's right or left side, and whether it is desired to view the selected structures in a two-dimensional view or as a representation of a three-dimensional view. When all options are identified, the structures are displayed, 74, as requested. It should be noted that the three-dimensional representation of the Head and Neck Region, as displayed, may be rotated to any angle desired; FIG. 8 is a screen print of the same, exact settings, but with the subject's Head and Neck Region rotated so that a partial right view is presented; i.e., element 84 is exactly the same as element 74, except that it is presented at a different viewing angle.

Applicants greatly prefer to utilize different color schemes for the target tumor site, for functionally-related structures, and for structures to be avoided. As may be seen from FIGS. 7 and 8, applicants have selected a bright red for the target site, a darker or cherry red for connected structures, and a bright yellow for structures which should be avoided. One may, however, utilize any of a number of different color schemes without departing from the principles of the present invention. Since applicants expect their system to become the standard for radiation treatment planners, for clinicians, for surgeons and for emergency health care providers, however, undoubtedly many mistakes might be avoided in the future if all such users employ the same color coding system.

Figure 7:
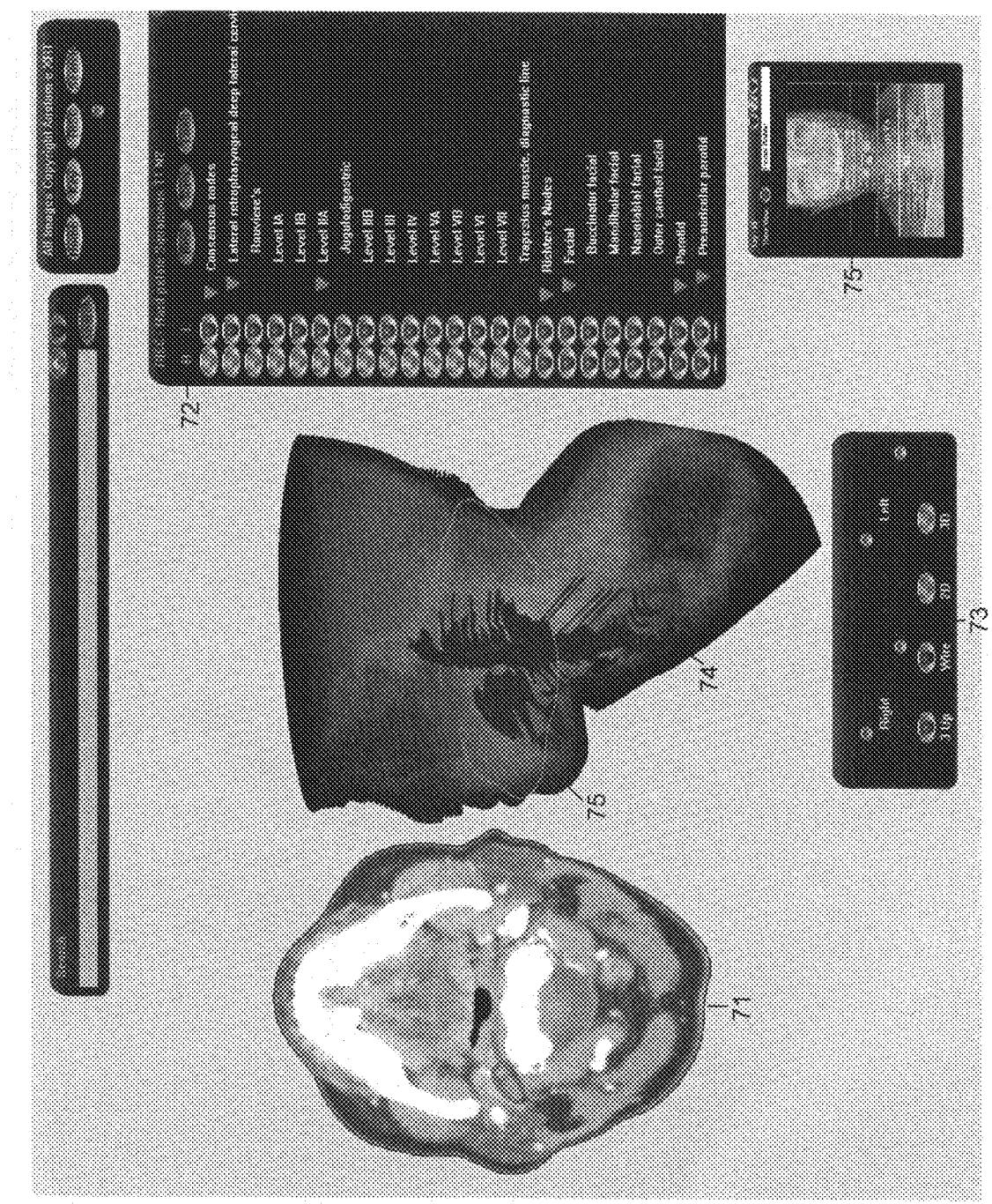
FIG. 7 is a screen print comprising a three dimensional representation of lymphatic tissue in the head and neck region, partial left view.

It may be noted that immediately below element 72 of FIG. 7 is a small display of a completed visual key of the present invention; wherever one may place the cursor and click, a temporary reference line (green line 75) is preferably displayed; simultaneously, the three-dimensional version of this same line is displayed in the three-dimensional representation of the standard reference, so that the user may see at a glance exactly where he is in the stack of images; simultaneously, the exact two-dimensional slice or image is displayed closely adjacent the three-dimensional view. The user may rapidly navigate through the one hundred or so images by moving his cursor up or down, and clicking wherever desired; the user is not restricted to incrementing such views one by one, but may skip as many as desired to view the next image of interest. Simultaneously, the corresponding two-dimensional image will be immediately displayed, and that image's location in the three-dimensional view will be immediately depicted by a relocated green line.

Medical practitioners will immediately appreciate the sheer volume of the labor required to produce applicants' invention, as well as the amount of labor on the part of a user which such a system will save. In addition, practitioners such as radiation treatment planners will not only save a considerable amount of time but will be able to render a much higher quality of treatment. No longer will educated surmises have to be made as to proper treatment, or as to what a particular body part may be or do; instead, one will be able to see at a glance all the information needed to make a well-informed decision. For example, in one preferred embodiment a touch pen may then be conveniently used to (a) make sure the user understands exactly what body part is being presented and (b) to aid in treatment planning. Touching any particular body part displayed in one of the reference images 71 with a touch pen may present the name of that particular body part on the screen closely adjacent such pen, while simultaneously highlighting that name (and associated information) in the text portion of the database. If the user is a radiation treatment planner and has imported his patient images onto the same screen, he may use such a touch pen to draw the outline of the body part to be irradiated, on each image displaying such structure. When that task is completed, the planner may then consult the three-dimensional image 74 of connecting parts (cherry red) and decide which, if any, of such connected parts should also be treated. The planner himself may specify the connected parts of possible interest, as by clicking on the various buttons of element 72, or he may 'default' to a treatment plan of a leading institution; in either event, the appropriate structures will be displayed almost instantaneously. Should he not prefer the first default plan, he may quickly obtain the plans of other institutions for his consideration. Structures to be avoided are handled in a similar manner. Thus errors of omission due to incomplete information of connected structures should be eliminated, as should such errors regarding structures to be avoided.

Such treatment planners will also immediately appreciate the flexibility and convenience of the present invention, which may be used side-by-side with such physicians' present treatment systems. Even more conveniently, a patient's actual scans may be imported into applicants' system and displayed in a split screen fashion, or one may be superimposed upon the other, with either faded or heightened as desired, or with the user rapidly deleting one image and repeatedly recalling it in superposition to make his understanding of each and every body part of his patient complete, as well as most convenient and quick. When the planning physician is satisfied, the parts to be irradiated or avoided may be drawn on the screen in the conventional manner, and the resulting images exported back to his treatment planning computer system.

Still further, such a user will have available at his fingertips a complete library of 'best practice' treatments as performed by the nation's leading oncology institutions, and may utilize any of such differing treatment methods as he may deem warranted in any particular case, or may 'pick-and-choose,' i.e., combine partial treatments from one source with those of another, as his judgment warrants in any particular case. Once an institution standardizes its preferred method of treatment, the treatment which a patient receives will no longer be dependent upon the vagaries or personal preferences of individual physicians; rather, all patients with the same conditions will receive the same treatment—the institution's collective best judgment for best treatment. Further, both institutions and individual physicians may conveniently build libraries of different treatment procedures, simply by saving to memory each treatment plan drawn for each tumor analyzed, and have them available for future use or future monitoring of outcomes to determine which may actually prove best. In short, the present invention promises a new day in the practice of medicine.

Other, alternate forms of the present invention will suggest themselves from a consideration of the apparatus, systems, methods and principles herein-before discussed. Accordingly, it should be understood that the systems and techniques depicted in the accompanying drawings and described in the accompanying specification are intended solely as exemplary embodiments of the present invention and not as limitations thereto.

We claim:

1. A method of creating a computerized library of treatment plans for specific tumors, comprising the steps of identifying a source for at least one said treatment plan, specifying anatomical structures to be treated according to said treatment plan, and storing said specified structures in memory in association with said treatment plan and said specific tumor, whereby said plan may be recalled upon identifying said source and said specific tumor.

2. The method of claim 1, comprising the further step of highlighting said structures on a monitor for displaying said treatment plan.

3. The method of claim 1, comprising the further step of displaying images of said specified structures on a monitor for displaying said images.

4. The method of claim 3, wherein said images are representations of three-dimensional images.

5. The method of claim 3, wherein said images are wireframe images.

6. A system for creating a computerized library of treatment plans for specific tumors, comprising means for identifying a source for at least one said treatment plan, means for specifying anatomical structures to be treated according to said treatment plan, and means for storing said specified structures in memory in association with said treatment plan and said specific tumor.

7. The system of claim 6, further comprising means for highlighting said structures on a monitor for displaying said treatment plan.

8. The system of claim 6, further comprising means for displaying images of said specified structures on a monitor for displaying said images.

9. The system of claim 8, wherein said images are representations of three-dimensional images.

10. The system of claim 8, wherein said images are wireframe images.

11. A visual key to aid in the rapid identification of images of interest from a multiplicity of images, comprising a combination image of a registration image of a subject combined with a reference image of an exterior surface with anatomical features corresponding spatially to features of said registration image.

12. The visual key of claim 11, said combination image further comprising a set of fiducial lines constructed thereon, at least one of said fiducial lines corresponding to at least one physiological landmark of said subject.

13. The visual key of claim 12, wherein selection of a fiducial line may activate a desired radiological sectional image.

14. The visual key of claim 12, wherein selection of a fiducial line may activate a desired textual section of a medical information database.

15. The visual key of claim 12, wherein selection of an anatomical feature of said reference image may activate a desired sectional image.

16. The visual key of claim 12, wherein selection of an anatomical feature of said reference image may activate a desired textual section of a medical information database.

17. The visual key of claim 11, wherein said combination image further comprises color coded lines depicting clinically relevant information.

18. The visual key of claim 17, wherein lengths and positions of said color coded lines define boundaries of types of body systems.

19. The visual key of claim 18, wherein an additive color denotes an overlapping of the boundaries of types of body systems.

20. The visual key of claim 18, wherein selection of a colored line segment may activate a desired textual section of a medical information database.

21. The visual key of claim 17, wherein a pre-determined color indicates the positioning of at least a portion of a body system behind another portion of a body system.

22. The visual key of claim 17, wherein said color coded lines are super-imposed upon registration lines of said registration image, thereby presenting additional relevant information without degrading said combination image.

23. The visual key of claim 17, wherein groups of body systems are denoted by alphanumeric representations superimposed upon said combination image.

24. The visual key of claim 17, wherein selection of a colored line segment may activate a desired radiological sectional image.

25. The visual key of claim 11, wherein said reference image comprises a photographic image.

26. The visual key of claim 11, wherein said combination image comprises a registration image, a reference image, a vector graphic surface and selected information from a medical database.

27. The visual key of claim 11, wherein selection of a registration line of said registration image may activate a desired radiological sectional image.

28. The visual key of claim 11, wherein selection of a registration line of said registration image may activate a desired textual section of a medical information database.

29. The visual key of claim 11, wherein said registration image and said reference image are frontal images.

30. A method of constructing a visual key to aid in the rapid identification of images of interest from a multiplicity of images, comprising the step of combining a registration image of a subject with a reference image of an exterior surface with anatomical features corresponding spatially to features of said registration image.

31. The method of claim 30, further comprising the step of constructing a set of fiducial lines thereon, at least one of said fiducial lines corresponding to at least one physiological landmark of said subject.

32. The method of claim 31, comprising the further step of presenting a desired radiological sectional image by selecting a fiducial line.

33. The method of claim 31, comprising the further step of presenting a desired textual section of a medical information database by selecting a fiducial line.

34. The method of claim 31, comprising the further step of presenting a desired sectional image by selecting an anatomical feature of said reference image.

35. The method of claim 31, comprising the further step of presenting a desired textual section of a medical information database by selecting an anatomical feature of said reference image.

36. The method of claim 30, further comprising the step of adding color coded lines depicting clinically relevant information to said combination image.

37. The method of claim 36, comprising the further step of defining boundaries of types of body systems by positions and lengths of said color coded lines.

38. The method of claim 37, comprising the further step of indicating an overlapping of the boundaries of types of body systems by employing additive color for at least one of said color coded lines.

39. The method of claim 37, comprising the further step of presenting a desired textual section of a medical information database by selecting a colored line segment.

40. The method of claim 36, comprising the further step of indicating that at least a portion of a body system is positioned behind another portion of a body system by assigning a pre-determined color to at least one of said color coded lines.

41. The method of claim 36, comprising the further step of presenting additional relevant information without degrading said combination image by superimposing said color coded lines upon registration lines of said registration image.

42. The method of claim 36, comprising the further step of denoting groups of body systems by alphanumeric representations superimposed upon said combination image.

43. The method of claim 36, comprising the further step of presenting a desired radiological sectional image by selecting a colored line segment.

44. The method of claim 30, wherein said reference image comprises a photographic image.

45. The method of claim 30, comprising the further step of combining a vector graphic surface and selected textual information from a medical database.

46. The method of claim 30, comprising the further step of presenting a desired radiological sectional image by selecting a registration line of said registration image.

47. The method of claim 30, comprising the further step of presenting a desired textual section of a medical information database by selecting a registration line of said registration image.

48. The method of claim 30, wherein said reference image and said registration image are frontal images.

49. A method of creating a unified, computer searchable, medical database comprising the step of combining a reference anatomical textual database with a reference anatomical graphical database.

50. The method of claim 49, wherein said graphical database comprises at least one graphical representation of at least one individual body part.

51. The method of claim 50, wherein said body parts are assigned unique, computer readable identifiers.

52. The method of claim 51, wherein said identifiers are alphanumeric identifiers.

53. The method of claim 51, wherein said identifiers comprise a plurality of fields.

54. The method of claim 53, wherein related body parts are computer searchable by color.

55. The method of claim 50, wherein at least one of said graphical representations is represented internally by a geometric formula.

56. The method of claim 55, wherein at least one of said geometric formulas is a volumetric formula.

57. The method of claim 50, comprising the further step of using at least one vector graphic technique to represent at least one of said graphical representations.

58. The method of claim 57, wherein at least one of said vector graphic techniques is a Bezier technique.

59. The method of claim 50, wherein at least one individual body part is color coded.

60. The method of claim 59, wherein pre-selected characteristics of a user-selected body part are computer searchable by clicking on a movable cursor.

61. The method of claim 59, wherein pre-selected characteristics of a user-selected body part are computer searchable by depressing a keyboard key.

62. The method of claim 49, wherein said graphical database comprises at least one graphical representation of at least one group of body parts.

63. The method of claim 62, wherein said groups of body parts are assigned unique, computer readable identifiers.

64. The method of claim 63, wherein said identifiers are alphanumeric identifiers.

65. The method of claim 63, wherein said identifiers comprise a plurality of fields.

66. The method of claim 62, wherein at least one of said graphical representations is represented internally by a geometric formula.

67. The method of claim 66, wherein at least one of said geometrical formulas is a volumetric formula.

68. The method of claim 49, comprising the further step of identifying a major body region of interest and specifying body views of interest.

69. The method of claim 49, comprising the further step of identifying a tumor site and cell type of interest.

* * * * *